(12) United States Patent
Agvald et al.

(10) Patent No.: US 8,552,068 B2
(45) Date of Patent: *Oct. 8, 2013

(54) COMPOSITIONS AND METHODS

(76) Inventors: Per Agvald, Bagarmossen (SE); Dag Linnarsson, Stocksund (SE); Christofer Adding, Akersberga (SE); Lars Gustafsson, Hasselby (SE); Kristofer Nilsson, Huskvarna (SE)

(*) Notice: Subject to any disclaimer, the term of this patent is extended or adjusted under 35 U.S.C. 154(b) by 1011 days.

This patent is subject to a terminal disclaimer.

(21) Appl. No.: 10/573,335

(22) PCT Filed: Sep. 14, 2005

(86) PCT No.: PCT/SE2005/001336
§ 371 (c)(1),
(2), (4) Date: Aug. 11, 2008

(87) PCT Pub. No.: WO2006/031191
PCT Pub. Date: Mar. 23, 2006

(65) Prior Publication Data
US 2008/0293813 A1 Nov. 27, 2008

(30) Foreign Application Priority Data
Sep. 14, 2004 (SE) .................................... 0402221

(51) Int. Cl.
A01N 33/24 (2006.01)
A01N 37/00 (2006.01)
A01N 33/18 (2006.01)
A61K 31/13 (2006.01)
A61K 31/21 (2006.01)
A61K 31/04 (2006.01)

(52) U.S. Cl.
USPC ............ 514/645; 514/506; 514/509; 514/740

(58) Field of Classification Search
USPC .................... 514/645, 605, 509, 740
See application file for complete search history.

(56) References Cited

U.S. PATENT DOCUMENTS

| | | | |
|---|---|---|---|
| 5,646,181 A * | 7/1997 | Fung et al. ................ | 514/506 |
| 6,352,709 B1 | 3/2002 | Stamler et al. | |
| 6,417,162 B1 | 7/2002 | Garvey et al. | |
| 6,673,338 B1 | 1/2004 | Arnold et al. | |
| 6,737,447 B1 * | 5/2004 | Smith et al. ................ | 523/105 |
| 2002/0061879 A1 | 5/2002 | Garvey et al. | |
| 2002/0094985 A1 | 7/2002 | Herrmann et al. | |
| 2003/0050305 A1 | 3/2003 | Tejada | |
| 2004/0162243 A1 | 8/2004 | Marek et al. | |

FOREIGN PATENT DOCUMENTS

| | | |
|---|---|---|
| EP | 1023900 A2 | 8/2000 |
| WO | WO-94/22482 A1 | 10/1994 |
| WO | WO-96/35416 A1 | 11/1996 |
| WO | WO-96/38136 A1 | 12/1996 |
| WO | WO-99/67296 A1 | 12/1999 |
| WO | WO-00/57891 A1 | 10/2000 |
| WO | WO-2004/026345 A1 | 4/2004 |

OTHER PUBLICATIONS

Definition of "substantially" from the Merriam Webster Online Dictionary [online], [Retrieved on Jun.23, 2009]. Retrieved from the internet <http://www.merriam-webster.com/dictionary/substantially>.*
Mailhes, J.B., Young, D., London, S.N. (1997) 1,2-Propanediol-Induced Premature Centromere Separation in Mouse Oocytes and Aneuploidy in One-Cell Zygoes. Biology of Reproduction, vol. 57, p. 92-98.*
Steven Godin, C., He, J., Drerup, J.M., Wyman, J. (1995) Effect of propylene glycol 1,2-dinitrate on cerebral blood flow in rats: a potential biomarker for vascular headache? Toxicology Letters, vol. 75, p. 59-68.*
Lindberg, L., Rydgren, G. (1998) Production of nitrogen dioxide in a delivery system for inhalation of nitric oxide: a new equation for calculation. British Journal of Anaesthesia, vol. 80, p. 213-217.*
Feelisch, M. (1998) The use of nitric oxide donors in pharmacological studies. Naunyn-Schmiedeberg's Archives of Pharmacology, vol. 358, p. 113-122.*
International Search Report mailed Jan. 30, 2006, for PCT application No. PCT/SE2005/001336, filed Sep. 14, 2005.

* cited by examiner

*Primary Examiner* — Scarlett Goon
(74) *Attorney, Agent, or Firm* — Morrison & Foerster LLP

(57) ABSTRACT

Gaseous nitric oxide (NO) can be delivered to a mammal for prophylactic or therapeutic purposes using a composition capable of delivering NO, comprising a compound capable of forming a reversible bond or association with NO. Methods for the manufacture and use of said composition are disclosed.

3 Claims, 13 Drawing Sheets

Muscle emboli challenge, survival at 60 min

COMPOSITIONS AND METHODS

CROSS REFERENCE TO RELATED APPLICATIONS

This application is a U.S. National phase Application of International Application No. PCT/SE2005/001336, filed Sep. 14, 2005, which claims priority to Swedish Application No. SE 0402221, filed Sep. 14, 2004, the contents of which are hereby incorporated by reference in the present disclosure in their entirety.

FIELD OF THE INVENTION

The present invention relates to compositions and methods for use in the delivery of gaseous nitric oxide (NO) to a mammal, preferably to a human, in need thereof. The present invention further relates to the use of gaseous NO, in combination with other substances, for the manufacture of pharmaceutical compositions. The invention also relates to methods for the prevention, treatment or alleviation of diseases where the administration of gaseous NO has a beneficial effect.

BACKGROUND OF THE INVENTION

Embolism

An experimental model of pulmonary embolism was used by the inventors to study the utility of different compositions with regard to the delivery of gaseous NO. Therefore, and with the aim to facilitate the understanding of the invention, background information about embolism is given below. The invention is however applicable to the prevention, alleviation or treatment of any condition, where the delivery of nitric oxide is beneficial, for example through its vasodilatory effects. The below background is thus given for illustrative purposes only, and it is not to be interpreted as limiting the scope of the invention.

An embolus is a foreign object, a quantity of air or gas, a fat globule, a bit of tissue or tumour, or a piece of a thrombus that circulates in the bloodstream until it becomes lodged in a vessel, partially or completely obstructing blood flow.

Pulmonary embolism is a common disorder accompanied by a significant morbidity and mortality. Thromboembolism may either be acute through activation of the blood clotting system and disseminated intravascular coagulation, or occur at a later stage through the formation of thrombi in the pulmonary vessels or formation in the venous circulation with subsequent embolization to the lung. The cause behind thrombi in the lung can also be so called thrombotisation, i.e. the formation of microthrombi in the circulation, triggered by tissue factors in the blood vessels. These microthrombi travel in the circulation until becoming trapped in the capillaries in the lung. It is estimated that up to 40% of all cases of pulmonary embolism may be of this origin.

It is also estimated that pulmonary embolism is the main or at least a contributory cause of in-patient death. Swedish autopsy records indicate that pulmonary embolism is involved in about 20% of in-patient deaths. Pregnant women, and in particular women undergoing caesarian section; cancer patients; trauma victims, and patients undergoing surgery, e.g. orthopedic surgery, are at risk. Further risk groups include, but are not limited to, individuals confined to bed rest or other types of confinement or restriction in the movement of the body or limbs, both during medical treatment or recovery from such treatment, or during transportation, e.g. air travel. Still further risk groups include, but are not limited to patients with infections, suffering from diseases or undergoing pharmaceutical treatments disturbing the blood clotting system or the system for resolution of blood clots.

One special form of pulmonary embolism, pulmonary gas embolism, is a well-known consequence of surgery, trauma, diving and aviation, including the exploration of space. Another form, pulmonary thromboembolism, is caused when a thrombus or fat globule travels in the blood to the lungs as a result of trauma, surgery or dislodging of a thrombus or part thereof from another location in the body, e.g. in deep venous thrombosis (DVT).

In the majority of the cases of pulmonary embolism, the source is deep venous thrombosis (DVT). Venous thromboembolic disease is the third most common cardiovascular disease after ischemic coronary heart disease and stroke. The most common treatments of pulmonary embolism include the administration of nasal oxygen, infusion of anticoagulantia and/or trombolytica, and surgical intervention. In the administration of thrombolytica, bleeding is a serious complication, which has to be considered. Inhaled nitric oxide (NO) has been tried experimentally in pulmonary embolism, but consensus has not been reached if such treatment is efficacious or not.

The pathophysiology of pulmonary embolism is pulmonary macro- or micro-obstruction, depending on emboli size, leading to pulmonary hypertension of varying severity. Acute pulmonary hypertension may cause right ventricle failure (acute cor pulmonale) and eventually cardiogenic chock. Treatment of acute pulmonary hypertension must therefore include reduction of pulmonary afterload, preferably pulmonary vasodilators with no systemic effects. Another feature of pulmonary embolism is disturbances of blood gases of varying degree, indicating ventilation-perfusion matching failure, though normal or disturbed blood gases are not conclusive for pulmonary embolism. For example, $PaO_2$ is likely to be decreased after acute massive pulmonary embolism but may be normal in patients with sub-massive pulmonary embolism.

For more information on pulmonary embolism, see "Guidelines on diagnosis and management of acute pulmonary embolism", Task Force on Pulmonary Embolism, European Society of Cardiology, European Heart Journal 2000; 21:1301-1336.

Insufficient perfusion also occurs in other instances, such as transplantation and in individuals confined to bed rest or other types of confinement or restriction in the movement of the body or limbs, both during medical treatment or recovery from such treatment, or during transportation, e.g. air travel.

Nitric Oxide

Nitric oxide (NO) is a molecule of importance in several biological systems, and is continuously produced in the lung and can be measured in ppb (parts per billion) in expired gas. The discovery of endogenous NO in exhaled air, and its use as a diagnostic marker of inflammation dates back to the early 1990-ies (See e.g. WO 93/05709; WO 95/02181). Today, the significance of endogenous NO is widely recognized, and since a few years back, a clinical analyzer is available on the market (NIOX®, the first tailor-made NO analyzer for routine clinical use with asthma patients, AEROCRINE AB, Solna, Sweden).

In the summer of 1997 the European Respiratory Journal published guidelines (ERS Task Force Report 10:1683-1693) for the standardization of NO measurements in order to allow their rapid introduction into clinical practice. Also the American Thoracic Society (ATS) has published guidelines for clinical NO measurements (American Thoracic Society, Medical Section of the American Lung Association Recommendations for standardized procedures for the online and offline measurement of exhaled lower respiratory nitric oxide and nasal nitric oxide in adults and children—1999, in *Am J Respir Crit. Care Med,* 1999; 160:2104-21 17).

In early experiments attempting to elucidate the role of NO in respiratory gas, massive helium or air emboli were used to stop the circulation in the lungs of test animals. The results indicated that increased levels of NO could be detected in exhaled air (Gustafsson et al., Endogenous nitric oxide is present in the exhaled air of rabbits, guinea pigs and humans. Biochem Biophys Res Commun 1991; 181:852-7).

In 1999, Deem et al. published results indicating that haemodilution during venous gas embolization improves gas exchange, without altering V(A)/Q or pulmonary blood flow distributions (Anesthesiology., 1999 December; 91(6):1861-72). A continuous infusion of nitrogen through the left internal jugular vein at a rate of approximately 0.006 ml/kg min was applied to achieve embolization. In the results, an increase of NO is recorded in embolised, haemodiluted anemic test animals, but not in undiluted controls. The authors state that the difference between baseline and T 1 VNO was statistically significant only for anemic animals. In practice, no increase in NO was recorded for animals with normal hematocrit. Deem et al. also discuss the limitations of the model, venous gas embolization using a continuous infusion of small bubbles, and states that it may be dissimilar to cases of air embolization in the clinical setting, and that extrapolation of the data to clinical management is difficult.

Thθ effect of vasodilator therapy was investigated in a canine model of acute pulmonary hypertension (Priebe, Am. J. Physiol. 255 (Heart Circ. Physiol, 24):H1232-H1239, 1998). In this study, pulmonary embolization was simulated by injecting a suspension of finely chopped muscle tissue in saline containing 2000 U of heparin. Small volumes (0.5-2 ml) of the muscle suspension was injected repeatedly through a femoral vein catheter until the mean pulmonary arterial pressure had increased approximately threefold.

It is generally recognised that endogenous generation of the gaseous molecule nitric oxide (NO) plays an important role in the modulation of pulmonary vascular tone to optimise ventilation-perfusion matching (Persson et al. 1990). In healthy human adults, NO is of importance in regulation of both basal pulmonary and systemic vascular resistance (Stamler et al. 1994). Local regulation of blood flow is influenced by administration of NO synthase inhibitor in healthy human subjects (Rimeika et al 2004). Vasodilator effects of endogenous NO in the postnatal pulmonary circulation clearly contribute to the adaptations of the fetal lung to air breathing at delivery (Abman et al. 1990). NO generation in the postnatal lung is stimulated for example by mechanical stretch, increased shear forces and increased $O_2$ tension in the alveoli (Heymann 1999). Measuring NO in exhaled breath is a good way of monitoring changes in endogenous NO production or scavenging in the lung (Gustafsson et al. 1991).

Since ventilation-perfusion matching disturbances and increased pulmonary artery blood pressure are features of pulmonary embolism, inhaled NO has been tested as treatment. Nevertheless treating pulmonary embolism with inhaled NO has yielded conflicting results e.g. improvement of hemodynamics but no improvement of blood gases (Tanus-Santos J E & Theodorakis M J, 2002).

Further, U.S. Pat. No. 5,670,177 discloses a method for treating or preventing ischemia comprising administering to a patient by an intravascular route a gaseous mixture comprising NO and carbon dioxide $CO_2$ wherein the NO is present in an amount effective to treat or prevent ischemia.

U.S. Pat. No. 6,103,769 discloses a similar method, with the difference that saline, saturated with NO, is used.

The published international application WO 94/16740 teaches the use of NO delivering compounds, such as S-nitrosothiols, thionitrites, thionitrates, sydnonimines, furoxans, organic nitrates, nitroprusside, nitroglycerin, iron-nitrosyl compounds, etc, for the treatment or prevention of alcoholic liver injury.

Nitrates are presently used to treat the symptoms of angina (chest pain). Nitrates work by relaxing blood vessels and increasing the supply of blood and oxygen to the heart while reducing its workload. Examples of presently available nitrate drugs include:

Nitroglycerin (glyceryl nitrate) (1,2,3-propanetriol-nitrate), which is today mostly taken sublingually to curb an acute attack of angina. Strong headaches and dizziness due to the rapid and general vasodilatory effect are frequently encountered side-effects. Nitroglycerin infusion concentrates are also available, and diluted in isotonic glucose or physiological saline for intravenous infusion.

Isosorbide mononitrate (1,4:3,6-dianhydo-D-glucitol-5-nitrate), which is taken as prophylactic against angina pectoris. Tolerance development is a problem in long-term treatment regimens. Frequent side-effects include headache and dizziness, as encountered with nitroglycerin.

Isosorbide dinitrate (1,4:3,6-dianhydo-D-glucitol-2,5-nitrate), which is taken both acutely and prophylactically against angina pectoris and cardiac insufficiency.

Pentaerythrityl nitrates, a group of organic nitrate, are known to exert long-term antioxidant and anti-atherogenic effects by as yet unidentified mechanisms. Pentaerythrityl tetranitrate has been investigated in the context of nitrate tolerance, an unwanted development in nitrate therapy, and experimentally tested in pulmonary hypertension.

Inorganic nitrates, such as potassium nitrate and sodium nitrate, have a long use as food preservatives. Nitrate has in general been considered to be potentially harmful, due to the theoretically possible formation of carcinogenic N-nitroso compounds in food, and in humans in vivo. Lately, the role of dietary nitrate has been reevaluated, in particular as the endogenous production of NO in the arginine-nitric oxide system and its role in host defense has been discovered.

L-arginine, and esters thereof, such as the ethyl-, methyl- and butyl-L-arginine have been used to increase the endogenous production of NO.

Among the compounds and compositions presently available, many are associated with undesired properties or side-effects, such as toxicity problems, stability problems, delayed action, irreversible action or prolonged action, etc.

One objective behind the present invention was to identify new compositions and method for the delivery of NO, or for providing a source of NO, in the treatment, alleviation and/or prevention of conditions, where the administration of NO is believed to be beneficial. One illustrative example of such conditions is insufficient perfusion, as exemplified by particular pulmonary embolism.

Another objective was to identify a method and composition, which makes it possible to administer NO in a safe and efficient fashion, and which does not exhibit the side effects or tolerance development associated with conventional treatments and drugs.

Other objectives, the solutions reached and the advantages associated therewith will become evident upon study of the description and examples.

SUMMARY OF THE INVENTION

The present inventors surprisingly found that a composition, capable of delivering nitric oxide (NO) can be used to increase perfusion in an organ, here exemplified by the lung in a model of pulmonary embolism. The invention is however not limited to the examples given, but has relevance and utility in the treatment of any condition where the administration of NO is beneficial.

Consequently, the inventors make available methods and compositions as defined in the attached claims, incorporated herein by reference.

SHORT SUMMARY OF THE DRAWINGS

The invention will be described in closer detail in the following description, examples, and attached drawings, in which FIG. 1 shows the changes in mixed exhaled nitric oxide ($FEN_O$) in artificially ventilated pentobarbital anaesthetized rabbits upon muscle emboli challenge (time 0). In group 1 (n=6, open circles and bar, 58 mg $kg^{-1}$ of muscle embolus (ME) was given and in group 2 with inhibited NO-production (n=4, L-NAME 30 mg $kg^{-1}$, closed circles and bars) 7.5 mg $kg^{-1}$ of embolus was given intravenously. The bars show the infusion times. * indicates p<0.05 compared to control levels (time=−5)

FIG. 2 shows changes in end-tidal $CO_2$ ($ETCO_2$) upon muscle emboli challenge (time 0) in artificially ventilated pentobarbital anaesthetized rabbits. Group 1 (n=6, open circles and bar, 58 mg $kg^{-1}$) and in group 2 with inhibited NO-production (n=4, L-NAME 30 mg $kg^{-1}$, closed circles and bars, 7.5 mg $kg^{-1}$). The bars show the infusion times. "¾" and "²⁄₄" indicates survival in group 2 (L-NAME group) at the indicated time points.

FIG. 3 shows changes in mean arterial blood pressure (MAP) upon muscle emboli challenge (ME, time 0) in artificially ventilated pentobarbital anaesthetized rabbits. Group 1 (n=6, open circles and bar, 58 mg $kg^{-1}$) and in group 2 with inhibited NO-production (n=4, L-NAME 30 mg $kg^{-1}$, closed circles and bars, 7.5 mg $kg^{-1}$). The horizontal bars labeled ME show the infusion times. "¾" and "²⁄₄" indicates survival in group 2 (L-NAME group) at the indicated time points.

FIG. 4 shows changes in heart rate (HR) upon muscle emboli challenge (time 0) in artificially ventilated pentobarbital anaesthetized rabbits. Group 1 (n=6, open circles and bar, 58 mg $kg^{-1}$) and in group 2 with inhibited NO-production (n=4, L-NAME 30 mg $kg^{-1}$, closed circles and bars, 7.5 mg $kg^{-1}$). The horizontal bars labelled ME show the infusion times for the muscle embolism challenge. "¾" and "²⁄₄" indicates survival in group 2 (L-NAME group) at the indicated time points.

Figure 9:
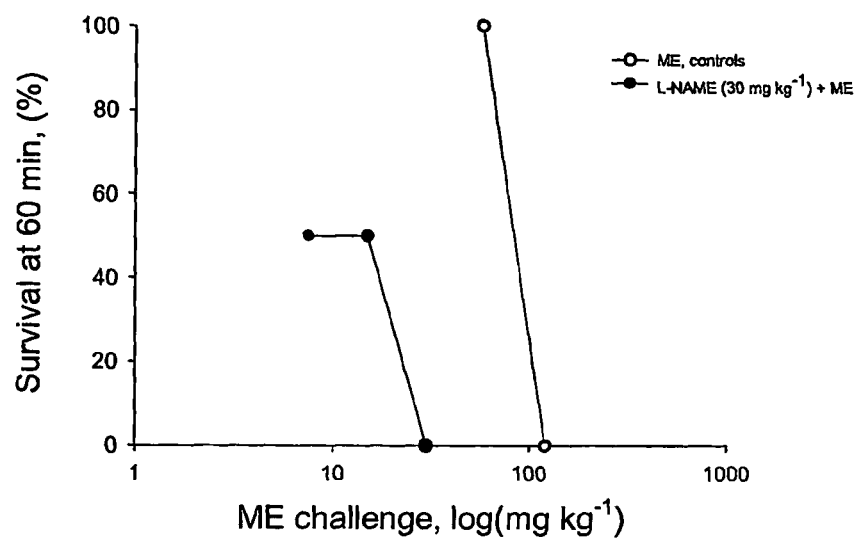

FIG. 9 shows percent survival in unpretreated control animals (artificially-ventilated pentobarbital anaesthetized rabbits) (open circle, n=6 and 2 for 58 and 120 mg $kg^{-1}$ respectively) receiving muscle embolus challenge (ME) at 58 to 120 mg $kg^{-1}$, and in animals receiving 7.5 to 30 mg $kg^{-1}$ muscle embolus challenge after pre-treatment with L-NAME (30 mg $kg^{-1}$; filled circle, n=4, 2 and 2 for 7.5, 15 and 30 mg kg-1 respectively).

Figure 10:
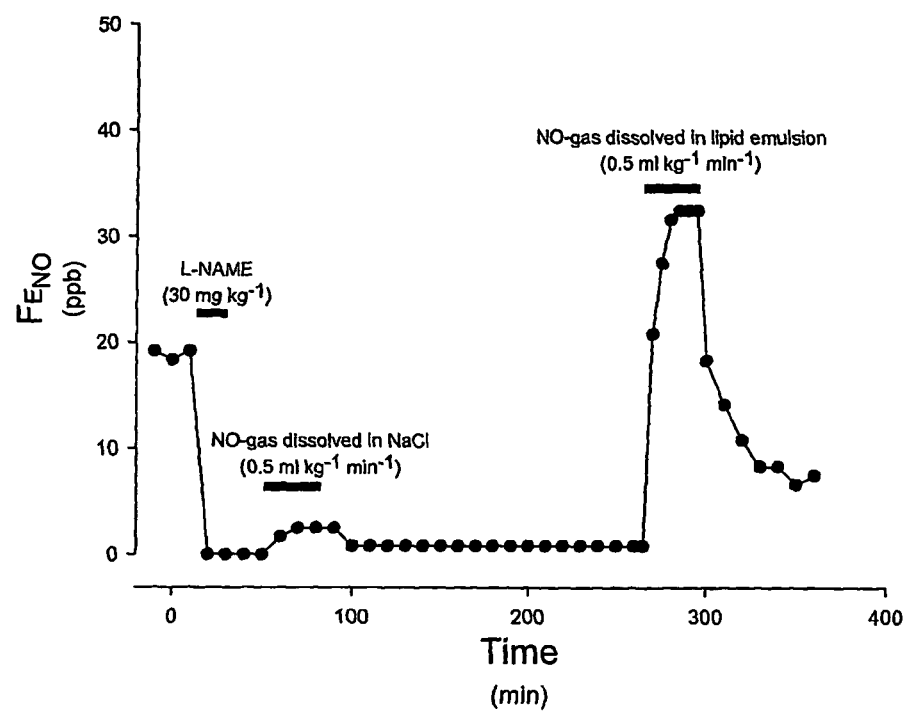

FIG. 10 is a graph showing changes in mixed exhaled nitric oxide ($FEN_O$) in artificially-ventilated pentobarbital anaesthetized rabbits upon infusions of NO-gas dissolved in either saline or lipid emulsion in an animal with inhibited NO-production (L-NAME 30 mg $kg^{-1}$, closed circles and bars. The bars show the infusion times.

Figure 11:
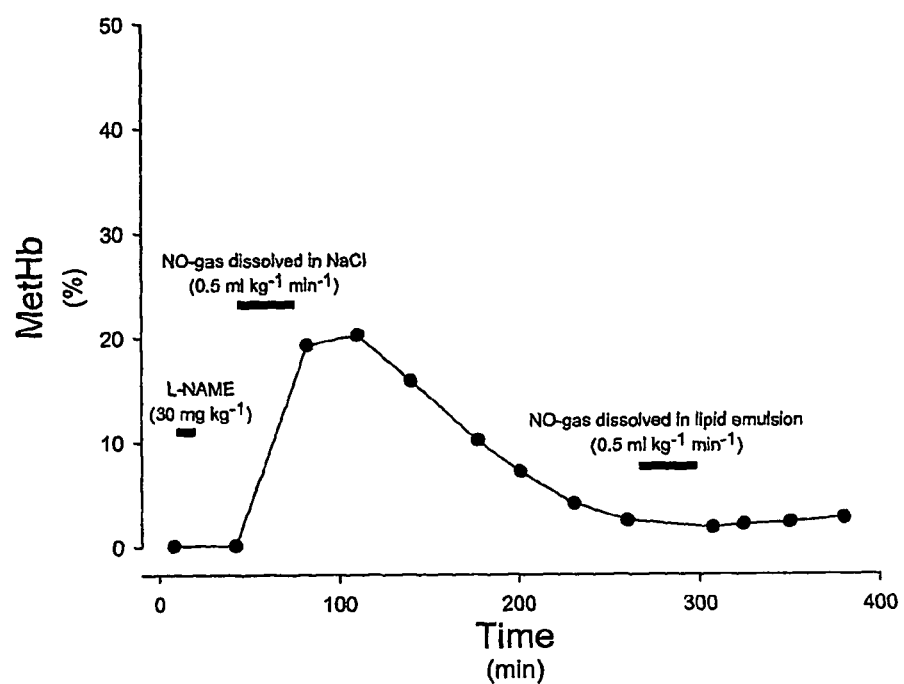

FIG. 11 is a graph showing changes in metHb in arterial blood in artificially-ventilated pentobarbital anaesthetized rabbits upon infusions of NO-gas dissolved in either saline or lipid emulsion in an animal with inhibited NO-production (L-NAME 30 mg $kg^{-1}$, closed circles and bars. The bars show the infusion times.

Figure 12:
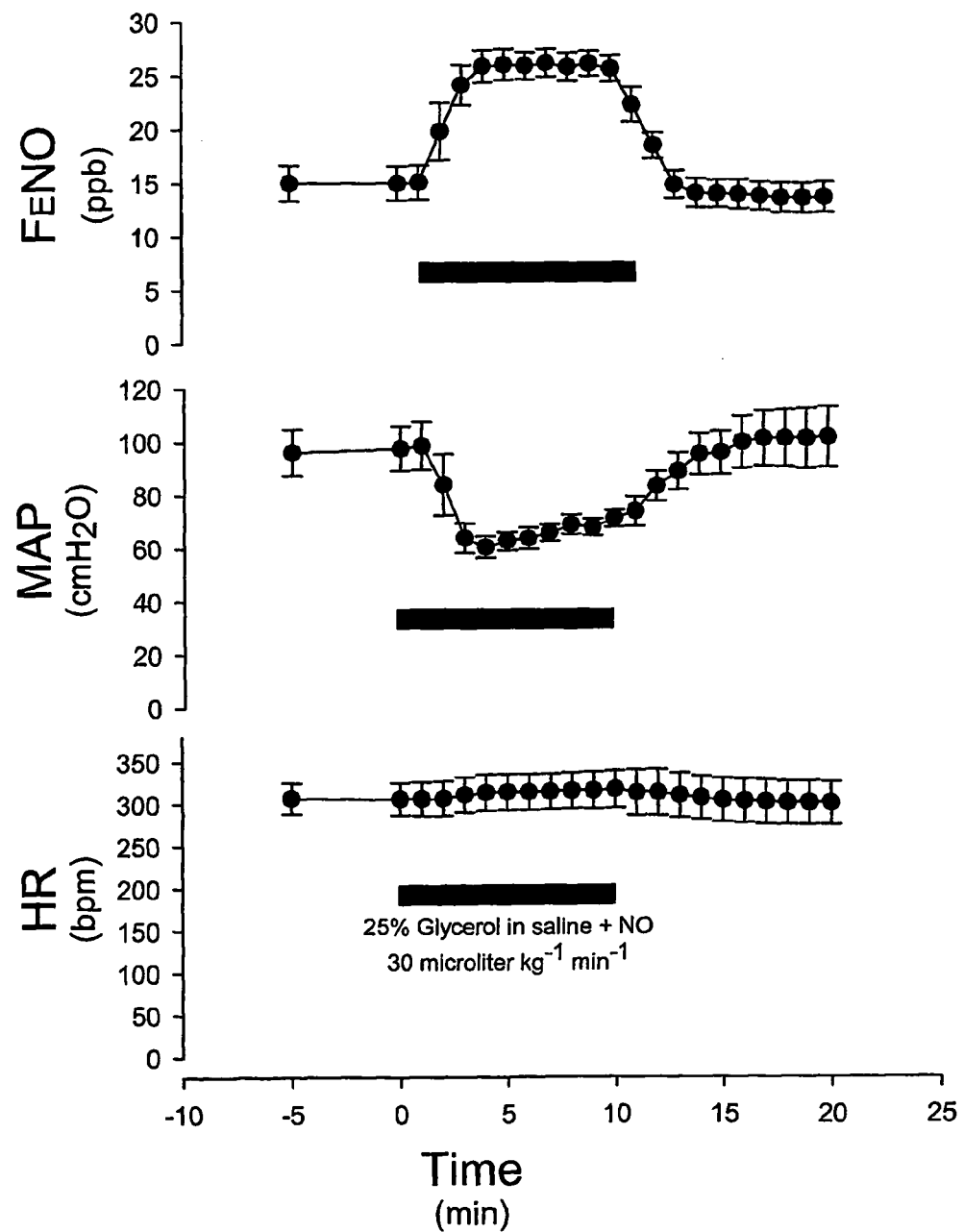

FIG. 12 relates to experiments with artificially ventilated pentobarbital anesthetized rabbits (n=4-5). The graphs shows the changes in mixed exhaled nitric oxide (FENO), mean arterial blood pressure (MAP) and heart rate due to intravenous infusion (30 microliter $kg^{-1}$ $min^{-1}$) of 25%-glycerol-NO. The bars show the infusion times.

Figure 13:
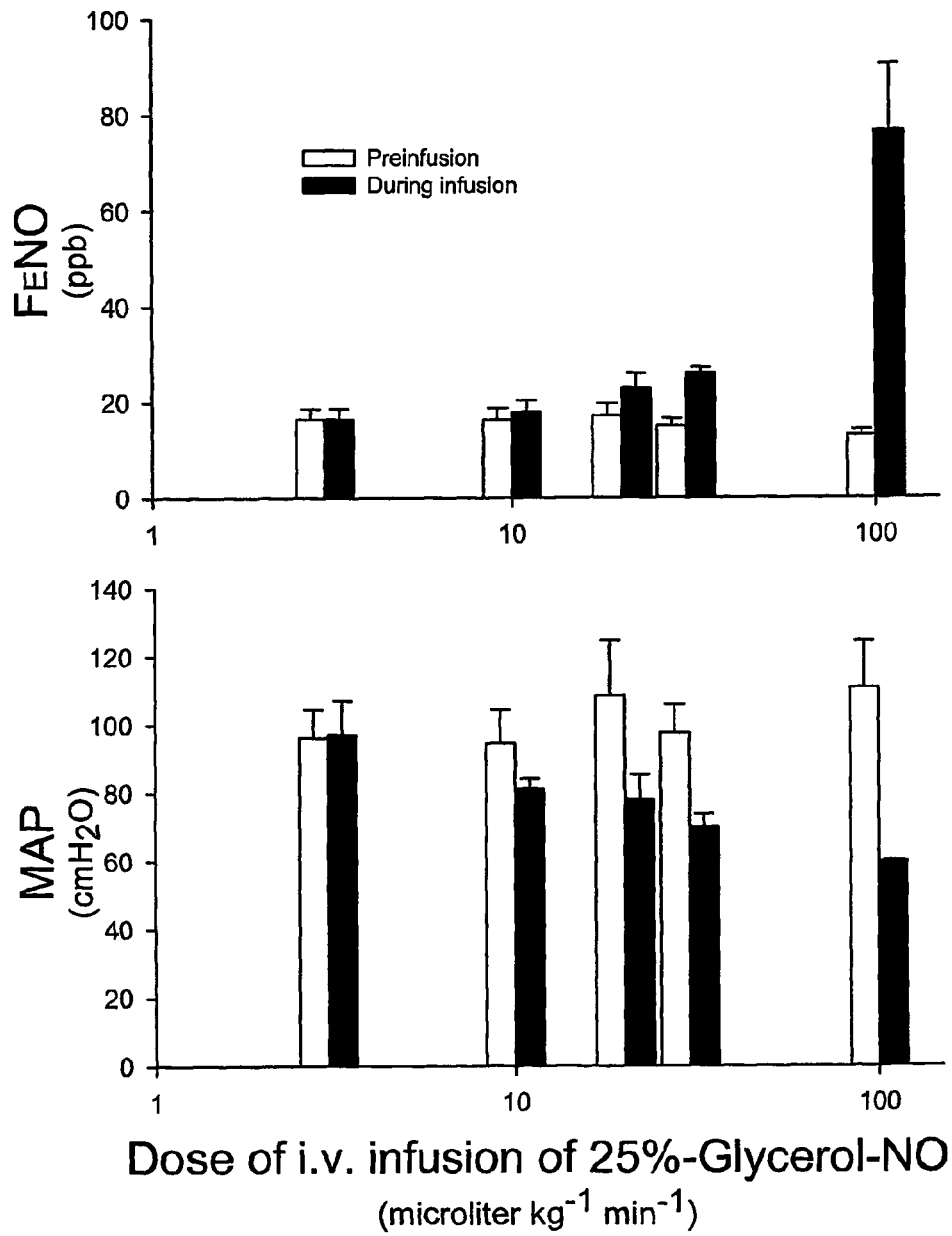

FIG. 13 relates to experiments with artificially ventilated pentobarbital anesthetized rabbits (n=3-5). The bars show mixed exhaled nitric oxide (FENO) and mean arterial blood pressure (MAP) before infusion (open bars) and during intravenous infusion of 25%-glycerol-NO (filled bars).

Figure 14:
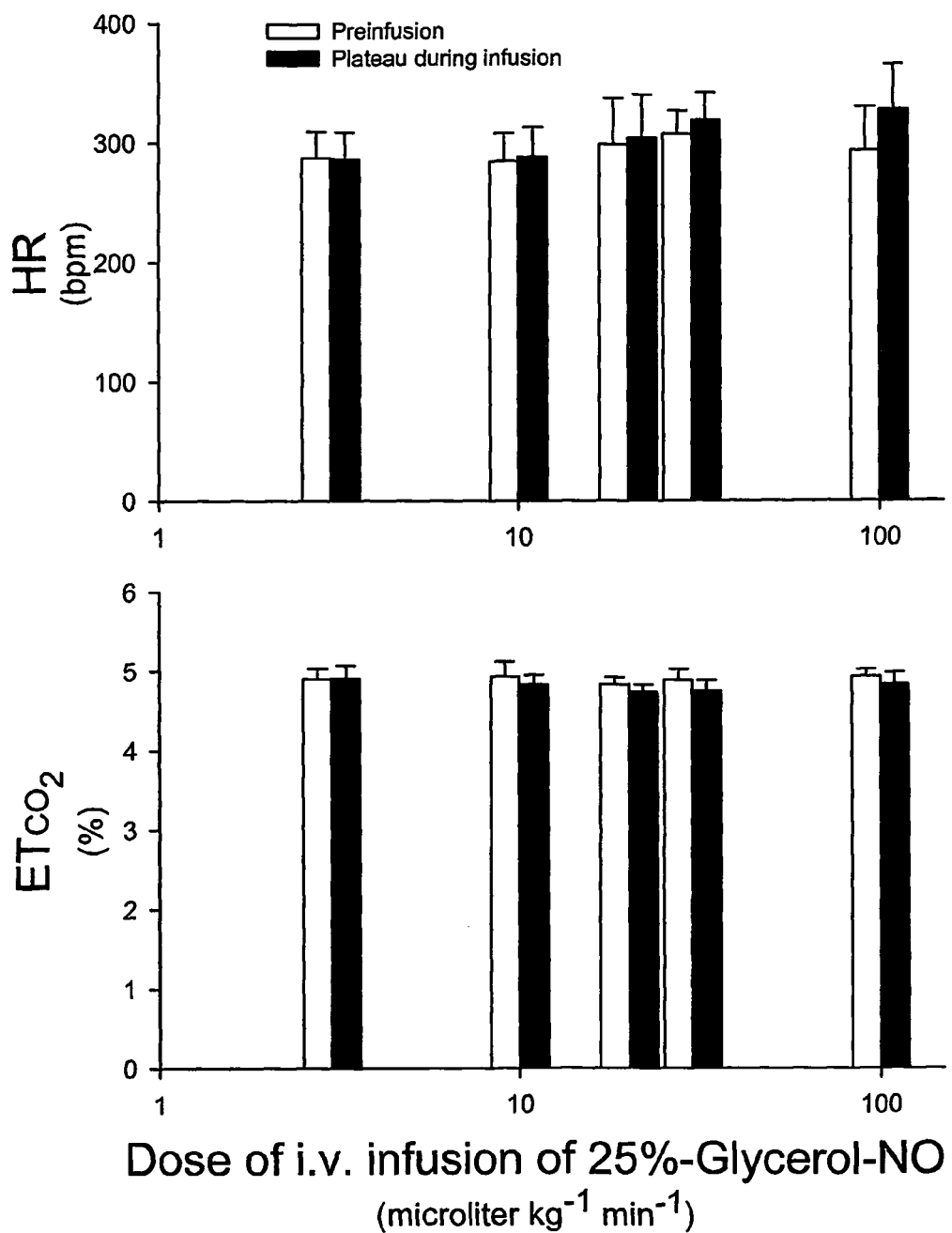

FIG. 14 relates to experiments with artificially ventilated pentobarbital anesthetized rabbits (n=3-5). The bars show heart rate (HR) and end-tidal $CO_2$ ($ETCO_2$) before infusion (open bars) and during intravenous infusion of 25%-glycerol-NO (filled bars).

Figure 15:
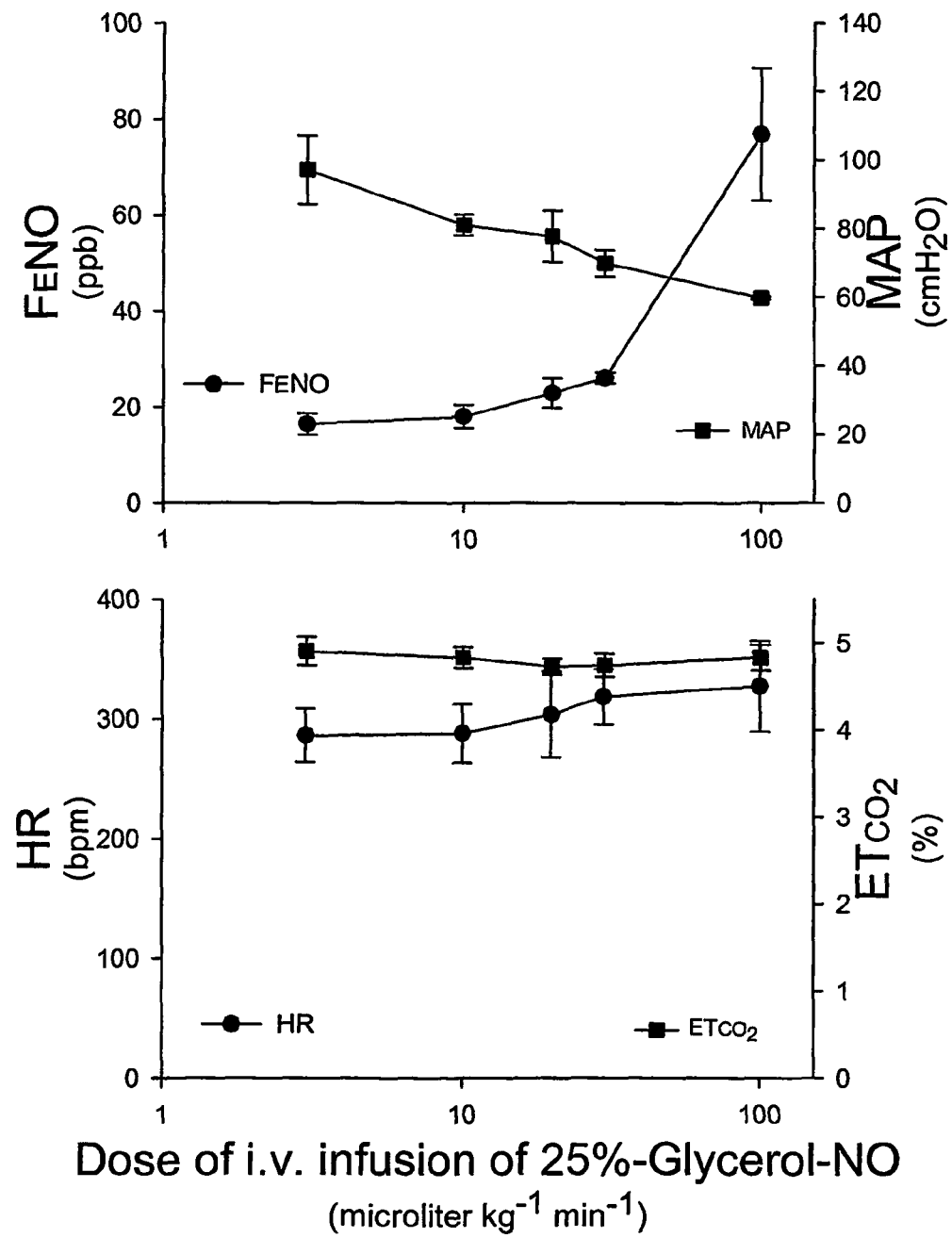

FIG. 15 relates to experiments with artificially ventilated pentobarbital anesthetized rabbits (n=3-5). The graphs show the dose and response relationships of mixed exhaled nitric oxide (FENO), mean arterial blood pressure (MAP), heart rate (HR) and end-tidal $CO_2$ ($EtcO_2$) due to intravenous infusion of 25%-glycerol-NO.

Figure 16:
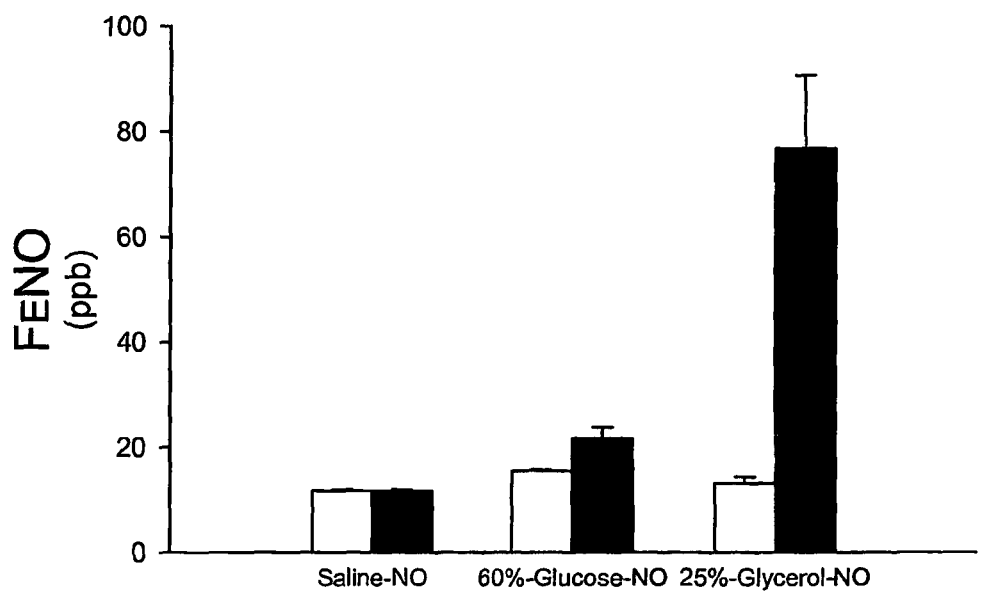
Figure 16:
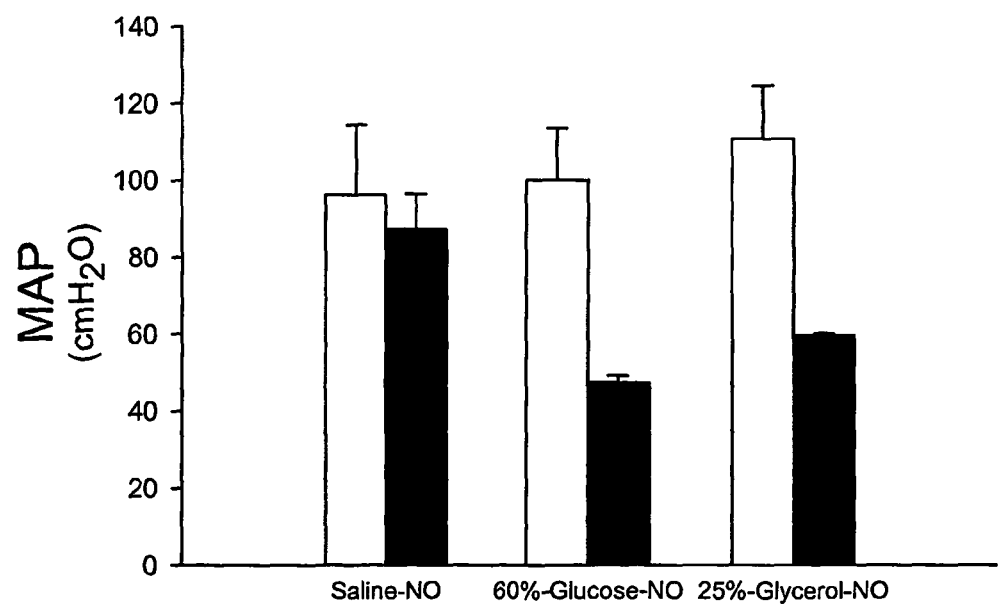

FIG. 16 relates to experiments with artificially ventilated pentobarbital anesthetized rabbits (n=2-3). The bars show mixed exhaled nitric oxide (FENO) and mean arterial blood pressure (MAP) before (open bars) and during intravenous infusion of nitric oxide (NO)-substitutions to different solutions (filled bars).

DESCRIPTION

Experiments performed by the present inventors indicate that the administration of inhaled NO is not a sufficient treatment in cases of pulmonary embolism. There are also numerous other conditions, where the administration of NO could be optimised, in order to improve the efficacy, reduce side effects or to achieve other beneficial effects.

The inventors performed experiments using gaseous NO dissolved in physiological saline, given as an injection of up to 5 ml per kg body weight. Surprisingly, no or only a very small increase of exhaled NO could be detected. Similarly, no changes in blood circulation were to be seen. This indicates that NO is rapidly decomposed or otherwise inactivated when infused in saline, or that it does not reach the lungs or the systemic vessels. This is supported by the observation of significant formation of methemoglobin (See FIG. 11) during infusion of NO in saline. Methemoglobin formation is an undesirable effect, since it decreases the oxygen-carrying capacity of blood.

The inventors then set out to find alternative and improved compositions for the administration of gaseous NO. It was highly surprising that NO could be formulated as lipid emulsion for intravenous administration, and that this formulation made it possible for the NO to reach the lungs. Experiments indicate that an infusion already of 0.1 to 0.5 ml/kg body weight results in clearly distinguishable increases in expired NO, in animals given L-NAME to inhibit the endogenous NO production.

The results also indicated that the infusion of NO in a lipid emulsion protected the animals against the lethal effects of pulmonary embolism in NO-synthesis inhibited animals. It is contemplated that the NO infusion exerts vasodilatory effects in the pulmonary circulation, and/or mild vasodilatory effect on systemic circulation, and inhibits thrombocyte aggregation, or a combination of these effects.

A surprising observation was that very little or no methemoglobin was formed during infusion of NO in a lipid emulsion (See FIG. 11). Further experiments, using other hydroxyl containing compounds (See below) indicated a favourably low or absent formation of methemoglobin.

The inventors then tested different compounds as carriers for gaseous NO. First, glycerol, a component of the lipid emulsion, was tested. Glycerol was surprisingly shown to act as a selective NO carrier. Further, other low molecular weight carbohydrates and their derivatives were tested. Analogs of glycerol, amino acids and polyethylene glycol were also tested. The results are presented below, in the experimental section, Table 1.

Consequently, the present invention makes available a composition for the delivery of gaseous nitric oxide (NO), comprising a compound capable of forming a reversible bond or association with NO. Such compounds have been identified and appear to be selective NO carriers. Without wishing to be bound by any theory, the inventors suggest that NO molecules become associated to these compounds when they are brought in contact in a substantially oxygen-free environment, and that the presence of at least one hydroxyl group is material for the association. Preliminary experiments indicate that the NO release mechanism is non-enzymatic, as judged from its release profile at different temperatures.

Said compound, capable of forming a reversible bond or association with NO, is preferably a water miscible organic compound, presenting at least one hydroxyl group.

According to one embodiment, said compound is a carbohydrate compound. According to another embodiment, said compound is a monosaccharide or a derivate thereof. Preferably, said compound is chosen among glucose, fructose, galactose, ribose. E.g. glucose can advantageously be used in the form of commercially available carbohydrate solutions for infusion, such as but not limited to Ringer-Glucose (Baxter), glucose solutions for infusion (manufactured by Baxter, Braun, Fresenius Kabi etc.).

According to another embodiment, said compound is a monosaccharide alcohol, preferably chosen among sorbitol and mannitol. E.g. mannitol can advantageously be used in the form of commercially available solutions for infusion, such as but not limited to Mannitol Baxter Viaflo® (Baxter) and Mannitol (Fresenius Kabi).

According to another embodiment, said compound is a modified monosaccharide, e.g. a compound chosen among fucose, 2-deoxy-ribose, and 1-O-methyl-ribose.

According to yet another embodiment, said compound is a disaccharide or a higher carbohydrate polymer of a monosaccharide or derivate thereof, and preferably a disaccharide or higher polysaccharide of glucose, fructose, galactose, ribose, sorbitol, mannitol, fucose, 2-deoxy-ribose, and 1-O-methyl-ribose, or one of sucrose, lactobionic acid, insulin, dextran, and fucoidan.

Based on the positive results obtained with mannitol and dextran, it is apparent that different formulations of carbohydrates, presently used as blood substituents and infusion solutions, fall within the scope of the present invention. Non-limiting examples include commercially available products such as Macrodex® and Rheomacrodex® (Meda), Ringer-Dextran® (Braun), HAES-Steril, HyperHAES, and Voluven® (Fresenius Kabi) and Hemohes® (Braun).

According to another embodiment, said compound is an alcohol or a derivate thereof. According to this embodiment, said compound is a monohydric alcohol, e.g. an alcohol chosen among 1-propanol, 2-propanol, sorbitol, and mannitol. According to another embodiment, said compound is a dihydric alcohol, e.g. 1,2-propanediol or 1,3-propanediol. According to yet another embodiment, said compound is a trihydric alcohol, e.g. glycerol.

According to yet another embodiment, said compound is a polymer of alcohol molecules or derivates thereof, e.g. polyethylene glycol of different molecular weight. Preliminary studies with PEG 400 have exhibited positive results.

According to another embodiment, said compound is a modified amino acid, peptide, polypeptide or protein. Preferably, and based on the current understanding of the mechanism of association between the compound and NO, said compound is a modified amino acid where the primary amino group has been substituted to a secondary amino group. One example is N-acetyl-cysteine. It is presently unclear if NO reacts with a thiol or another part of the molecule. It is however suggested that peptides, polypeptides or proteins that have been acetylated or otherwise conjugated, thus hiding the primary amine structure, can be used in the present invention.

According to another embodiment, said compound is albumin. Thus, according to the invention, albumin based blood substituents, such as but not limited to commercially available plasma substitutes and plasma protein infusion solutions, can be used. Examples include albumin infusion solutions (manufactured by Baxter, Behring, Octapharma etc.).

According to another embodiment, said composition is a lipid emulsion, such as emulsions and solutions for intravenous nutrition, here exemplified by Intralipid® (Fresenius Kabi). Other suitable emulsions are Clinoleic® (Baxter), Omegaven®, SMOFlipid® and Structolipid® (Fresenius Kabi), and Vasolipid® (Braun) and equivalent products.

The composition according to the invention is preferably formulated for topical, rectal, vaginal, intrauterine, intraurethral, intraurethral, intravesical, intra- or transcervical, intrauterine, laparoscopic, intrasurgical, nasal, ocular, sublingual, buccal, oral, enteral, intravenous, intraarterial, intratracheal, intramuscular or subcutaneous administration.

According to a preferred embodiment, the composition according to the invention contains substantially no oxygen. Further, according to another preferred embodiment, said composition capable of delivering gaseous NO is an injectable aqueous formulation containing gaseous NO substantially in the absence of oxygen.

Further, the present invention makes available a method for the treatment, alleviation or prevention of insufficient perfusion in an organ or organs in a human or animal patient, wherein a composition, capable of delivering NO is given intravenously to said patient. Insufficient perfusion includes states of insufficient perfusion of various etiology, in tissues or organs, including but not limited to transplanted tissues or organs, including organs or tissues intended for transplantation.

According to an embodiment of the invention, said insufficient perfusion is insufficient perfusion of a section or sections of a lung, due to pulmonary embolism. Pulmonary embolism includes pulmonary embolism of various etiology, including but not limited to pulmonary thromboembolism and pulmonary gas embolism.

Other indications, where the inventive composition is used either alone, or in combination with one or more pharmaceutical agents, acute pulmonary vasoconstriction of different genesis, pulmonary embolism, pulmonary hypertension of different genesis, including primary hypertension and secondary hypertension, systemic hypertension of different genesis, acute heart failure, acidosis, inflammation of the lung, adult respiratory distress syndrome, acute pulmonary edema, acute mountain sickness, asthma, hypoxia of different genesis, inflammation of different genesis, wound healing, and conditions where smooth muscle relaxation is needed.

The composition may also be used in situations where controlled hypotension is desired, e.g. controlled hypotension during neurosurgery.

The inventive composition is also preferably used alone, or in combination with one or more pharmaceutical agents, to act as an inhibitor of thrombocyte aggregation and coagulation, e.g. in combination with vasodilatation.

The inventive composition is also used as an adjunct to other pharmaceutically active agents, in order to increase their uptake, e.g. to increase the systemic uptake of topically administered systemic drugs; as an addition to injections, where increased local circulation is desired; as an adjunct to anti-tumor drugs and/or in conjunction with irradiation therapy, where a vasodilatory effect may increase the anti-tumor effects of the treatment.

According to an embodiment of this use, said insufficient perfusion in an organ or organs is insufficient perfusion of a section or sections of a lung, due to pulmonary embolism. Pulmonary embolism includes pulmonary embolism of various etiology, including but not limited to pulmonary thromboembolism and pulmonary gas embolism. Pulmonary hypertension, e.g. of the newborn, or primary or idiopathic pulmonary hypertension or pulmonary hypertension secondary to another disease or hypoxia can also be treated by means of the invention.

Thus, the present invention makes available first and second medical uses of the compounds identified above. In general terms, the invention makes available the use of a compound capable of forming a reversible bond or association with NO, for the manufacture of a pharmaceutical formulation for the treatment of a condition where the administration of NO is beneficial.

In the above first or second medical use, said compound is chosen among glucose, fructose, galactose, ribose, sorbitol, mannitol, fucose, 2-deoxy-ribose, 1-O-methyl-ribose, sucrose, lactobionic acid, insulin, dextran, fucoidan, 1-propanol, 2-propanol, 1,2-propanediol, 1,3-propanediol, glycerol, polyethylene glycol, N-acetyl-cysteine, albumin, and derivatives thereof.

According to the invention, said condition is chosen among inflammation, acute pulmonary vasoconstriction of different genesis, pulmonary embolism, pulmonary hypertension of different genesis, including primary hypertension and secondary hypertension, systemic hypertension of different genesis, acute heart failure, acidosis, inflammation of the lung, adult respiratory distress syndrome, acute pulmonary edema, acute mountain sickness, asthma, hypoxia of different genesis, inflammation of different genesis, wound healing, and conditions where smooth muscle relaxation is needed.

In the above, a pharmaceutical formulation is one of a plaster or bandage, a gel, a cream, an ointment, a solution, a suppository for topical, rectal or vaginal administration; a solution, for drop wise addition or for forming an aerosol for nasal or ocular administration; a solution, emulsion, drops, capsules or tablets for oral or enteral administration; an injectable solution or emulsion for intravenous, intraarterial, intratracheal, intramuscular or subcutaneous administration.

The present invention also makes available a method for the manufacture of a composition capable of delivering gaseous NO, wherein a aqueous solution, suitable for topical, rectal, vaginal, intraurethral, intravesical, nasal, ocular, sublingual, buccal, oral, enteral, intravenous, intraarterial, intratracheal, intramuscular or subcutaneous administration, is de-oxygenized until substantially free from oxygen, and then purged with pure NO gas until a desired NO concentration is reached.

In the method according to the invention, said compound capable of forming a spontaneously reversible association with NO is preferably a water miscible organic compound, presenting at least one hydroxyl group.

According to one embodiment, said compound is a carbohydrate compound. According to another embodiment, said compound is a monosaccharide or a derivate thereof. Preferably, said compound is chosen among glucose, fructose, galactose, ribose.

According to another embodiment, said compound is a monosaccharide alcohol, preferably chosen among sorbitol and mannitol.

According to another embodiment, said compound is a modified monosaccharide, e.g. a compound chosen among fucose, 2-deoxy-ribose, and 1-O-methyl-ribose.

According to yet another embodiment, said compound is a disaccharide or a higher carbohydrate polymer of a monosaccharide or derivate thereof, and preferably a disaccharide or higher polysaccharide of glucose, fructose, galactose, ribose, sorbitol, mannitol, fucose, 2-deoxy-ribose, and 1-O-methyl-ribose, or one of sucrose, lactobionic acid, insulin, dextran, and fucoidan.

As noted above, based on the positive results obtained with mannitol and dextran, it is apparent that different formulations of carbohydrates, presently used as blood substitutes and infusion solutions, fall within the scope of the present invention. Non-limiting examples include Macrodex® and Rheomacrodex® (Meda), Ringer-Dextran® (Braun), HAES-Steril, HyperHAES, and Voluven® (Fresenius Kabi) and Hemohes® (Braun).

According to another embodiment, said compound is an alcohol or a derivate thereof. According to this embodiment, said compound is a monohydric alcohol, e.g. an alcohol chosen among 1-propanol, 2-propanol, sorbitol, and mannitol. According to another embodiment, said compound is a dihydric alcohol, e.g. 1,2 propanediol or 1,3-propanediol. According to yet another embodiment, said compound is a trihydric alcohol, e.g. glycerol.

According to yet another embodiment, said compound is a polymer of alcohol molecules or derivates thereof, e.g. polyethylene glycol of different molecular weight. Preliminary studies with PEG 400 have exhibited positive results.

According to another embodiment, said compound is a modified amino acid, peptide, polypeptide or protein. Preferably, and based on the current understanding of the mechanism of association between the compound and NO, said compound is a modified amino acid where the primary amino group has been substituted to a secondary amino group. One example is N-acetyl-cysteine. As stated above, it is presently unclear if NO reacts with a thiol or another part of the molecule. It is however suggested that peptides, polypeptides or proteins that have been acetylated or otherwise conjugated, thus hiding the primary amine structure, can be used in the present invention.

According to another embodiment, said compound is albumin. Thus, according to the invention, albumin based blood substituents, such as but not limited to commercially available plasma substitutes and plasma protein infusion solutions, can be used. Examples include albumin infusion solutions (manufactured by Baxter, Behring, Octapharma etc.).

According to another embodiment, said composition is a lipid emulsion, such as emulsions and solutions for intravenous nutrition, here exemplified by Intralipid® (Fresenius Kabi). Other suitable emulsions are Clinoleic® (Baxter), Omegaven®, SMOFlipid® and Structolipid® (Fresenius Kabi), and Vasolipid® (Braun) and equivalent products.

The present invention also makes available a NO-saturated, substantially oxygen-free and physiologically acceptable composition, obtainable by a method as described above.

The composition according to the invention is preferably formulated as a plaster or bandage, a gel, a cream, an ointment, a solution, a suppository for topical, rectal, vaginal, intraurethral, or intravesical administration. It is preferably formulated as a solution, for drop wise addition or for forming an aerosol for nasal or ocular administration. It is preferably formulated as a solution, emulsion, drops, capsules or tablets for oral or enteral administration. It is preferably formulated as an injectable solution or emulsion for intravenous, intraarterial, intratracheal, intramuscular or subcutaneous administration.

When preparing the NO emulsion or specific carrier solution according to the present invention, it is important that the medium is de-oxygenized before addition of NO. Otherwise the added NO will be decomposed by oxygen. It is also necessary to use, store and administer the emulsion under exclusion of oxygen. In practice, the storage vessels, vials, bottles or bags, as well as the tubes and cannulas should be non-permeable to oxygen or at least have reduced permeability to oxygen. A skilled person can easily identify suitable packaging materials. Except for this consideration, conventional apparatuses and practices for administering pharmaceuticals can be used.

Advantages

One important clinical advantage of the present invention is that the effects of the gaseous NO, when administered to the patient in a composition according to the invention, will be most significant in hypoxic tissue. When gaseous NO formulated is given as an intravenous infusion, the risk of so called proximal steal, i.e. increased blood flow in neighboring healthy vessels, is avoided. This is a common side effect of vasodilating substances, leading to lowered blood pressure and related systemic symptoms.

Another advantage is that the manufacture of the inventive compositions is easy and requires no harsh conditions, which may alter or damage other components optionally present in the composition.

Yet another advantage is that the release of NO seems to be non-enzymatic, based on an experiment using a perfused lung model. A non-enzymatic release mechanism indicates that a composition according to the invention would avoid the tolerance development, associated with conventional NO-donating compositions.

Yet another advantage, especially in comparison with administration of NO in saline only, or NO in carbon dioxide, is the considerably lower formation of methemoglobin.

Further advantages will become evident to a skilled person upon study of the description and examples.

EXAMPLES

Methods

Anaesthesia and Initial Surgical Procedures

The experiments were approved by the local animal ethics committee. Male white New Zealand rabbits (n=20, body weight 2.456±0.086 kg) were anaesthetized via an ear vein with sodium pentobarbital, 6 mg ml$^{-1}$ in normal saline, 40-60 mg kg-1. The animals were placed in supine position and tracheotomised just below the cricoid cartilage to allow mechanical ventilation using a tracheal cannula with an outer diameter of 5 mm. The animals were ventilated by a Harvard Apparatus rodent ventilator (model 683, Harvard Apparatus, South Natick, Mass., USA). The ventilator was supplied with NO-free air using a charcoal filter (110×11 cm). Ventilation rate was 40 min$^{-1}$ at constant volume where the tidal volume was initially adjusted to keep the end-tidal CO2 at 4.5-5.3% as determined by a ventilatory monitor (Oscar-Oxy, Datex, Helsinki, Finland) sampling gas (150 ml min$^{-1}$, 15-20% of minute ventilation) from one of two side-arms connected to the tracheal cannula, and using a de-humidifying tube. The minute ventilation was 0.64-0.96 l min$^{-1}$. To the other side arm a pressure transducer (Statham, Hato Rey, Puerto Rico) was connected thus monitoring the insufflation pressure. The gas from the ventilator outlet was led through a switching valve to either of two beakers creating a positive end-expiratory pressure (PEEP) of 1-2 CmH$_2$O or 4-5 cmhbO. During the experiment the gas flow was altered between the lower PEEP (9 min) and the higher PEEP (1 min) with an interval of totally 10 min. A continuous infusion containing glucose (24.3 g l$^{-1}$), dextran 70 (26.5 g l$^{-1}$), NaHCO$_3$ (6.2 g l$^{-1}$), sodium pentobarbital (4.1 g l$^{-1}$) and pancuronium bromide (98 mg ml$^{-1}$) was administered at a rate of 5 ml kg$^{-1}$ h$^{-1}$ via the same ear vein by means of a Terumo STC-521 syringe pump (Terumo Corp., Tokyo, Japan). A heparinized catheter was inserted in the left common carotid artery for blood pressure and heart rate recordings (pressure transducer, Statham, Hato Rey, Puerto Rico), and arterial blood sampling. Another catheter was inserted in the right jugular vein for drug and muscle emboli administration. Body temperature was maintained at 37-38.5° C. by means of a heating pad connected to a thermostat. The muscles from the anterior compartment of the right lower hind limb were resected and placed in normal saline. Hereafter the animals were allowed a 30-60 min intervention-free period to obtain stable circulatory conditions and stable concentrations of expired NO.

NO Measurements in Exhaled Air

NO concentration, in mixed exhaled gas, was continuously measured by means of a chemiluminescence based system (Niox, Aerocrine AB, Solna, Sweden) sampling at 100 ml min$^{-1}$ at the end of a mixing chamber connected to the ventilator exhaust. The full mixing of expired air thus measured on was intermittently checked by monitoring CO2 concentration in the same chamber. In a few experiments, gas for NO measurement was sampled from the trachea at the same point as for tidal CO2 measurements, thus yielding breath by breath NO concentrations. Calibration was done using certified NO standard gas in nitrogen (AGA Specialgas, Lidingð, Sweden).

Preparation of Muscle Emboli

The resected muscle tissue was cleared from all visible connective tissue and then homogenized and dissolved in normal saline to a concentration of 0.1 g muscle ml$^{-1}$. 50 IE heparin per ml was added to the mixture. The homogenate was filtered through a filter (500 µm) to prevent clotting in the three way stop-cock.

Experimental Protocol

The animals were divided into two groups; 1) one group receiving a high dose (58 mg kg$^{-1}$) muscle homogenate and 2) a second group receiving the nitric oxide inhibitor L-NAME (30 mg kg$^{-1}$) 40 min before challenge with lower doses (30 to 7.5 mg kg$^{-1}$) muscle homogenate, since initial pilot experiments indicated a marked enhancement of emboli effects after L-NAME pretreatment. Blood samples were collected and analyzed for blood gases and acid-base status (ABL 300, Radiometer A/S, Copenhagen, Denmark) before L-NAME administration (group 2, time=−40 min) and shortly before muscle emboli challenge (group 1 and 2, time=−5 min). The muscle homogenate was infused by means of an infusion pump (CMA/100, Microinjection Pump, Carnegie Medicine AB, Stockholm, Sweden) with a flow of 150 µl kg$^{-1}$ min$^{-1}$ via a three way stop-cock into a carrier flow (864 Syringe Pump, Univentor LTD., Zejtun, Malta) of 150 µl kg$^{-1}$ min$^{-1}$ normal saline through the jugular vein catheter until full muscle emboli dose for each group was received. Arterial blood samples were collected and analysed at 10 min, 20 min, 40 min and 60 min after embolization. NO concentration in exhaled gas, end-tidal $CO_2$, heart rate, mean arterial pressure and insufflation pressure was continuously monitored on a Grass Polygraph (Grass Instruments Co, Quincy, Mass., USA) during the experiments.

Experiment on Intravenous Infusion of NO Dissolved in Lipid Emulsion

One rabbit pre-treated with L-NAME (30 mg kg$^{-1}$) received one infusion with NO-gas dissolved in normal saline and one with NO-gas dissolved in lipid emulsion (Intralipid®, Fresenius Kabi) through the catheter in the jugular vein without carrier flow. The infusion rate was for both liquids 0.5 ml kg$^{-1}$ min$^{-1}$. There was a recovery period between the two infusions for about 200 min.

The infusion liquids were created the same way. First the liquid was de-oxygenated for 20 min, in a gas-tight glass chamber with a rubber membrane with an inert gas; in this case helium gas, but nitrogen, argon etc could also be used. After this no oxygen were allowed to enter the liquid throughout the following procedure. The liquid was then purged with pure NO for a few minutes. The liquid was then collected through the rubber membrane in a gas-tight syringe with needle and from this syringe infused by means of syringe pump (864 Syringe Pump, Univentor LTD., Zejtun, Malta) in the jugular vein catheter.

Drugs

Heparin was purchased from Kabi Vitrum, Stockholm, Sweden, pancuronium bromide (Pavulon®) was from Organon, Oss, Holland, sodium pentobarbital was from Apoteksbolaget, Stockholm, Sweden and dextran 70 (Macrodex®) was from Pharmalink, Spanga, Sweden. L-NAME ($N^G$-nitro-L-arginine methyl ester) and routine chemicals were purchased from Sigma Chemical Company, St Louis, Mo., USA.

Statistics

Statistical data are given as mean and standard error of the mean (SEM). Statistical significance was calculated by means of repeated measurements ANOVA on ranks with Dunnet's post hoc analysis. $P<0.05$ was assigned as significance difference. All statistical calculations were done by using a computer program (SigmaStat, Jandel, San Rafael, Calif., USA).

Results in Experiments on Intravenous Infusion of NO Dissolved in Liquid Medium

Effects of L-NAME-Infusion

Infusion of L-NAME (30 mg kg$^{-1}$) throughout 10 min decreased exhaled nitric oxide (from 19 ppb to <1 ppb, FIG. 1), increased systemic mean arterial blood pressure (MAP, from 103 $CmH_2O$ to 128 cmHaO), and lowered heart rate (HR, from 274 beats min$^{-1}$ to 258 beats min$^{t1}$). End-tidal $CO_2$ and the relevant blood gas parameters were normal.

Infusion of NO-Gas Dissolved in Normal Saline

Figure 1:
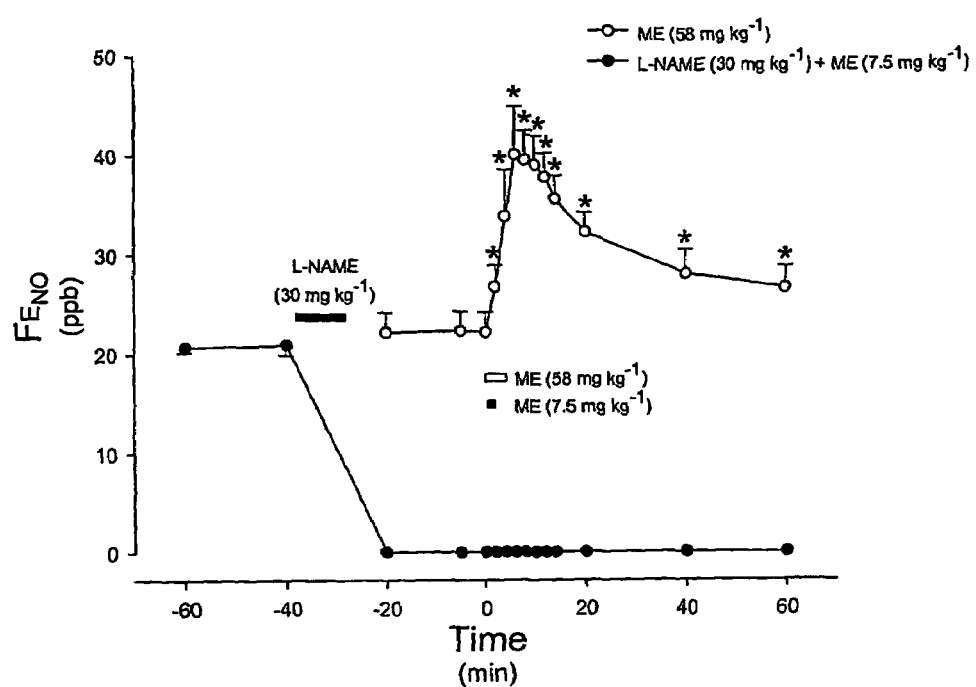
Figure 2:
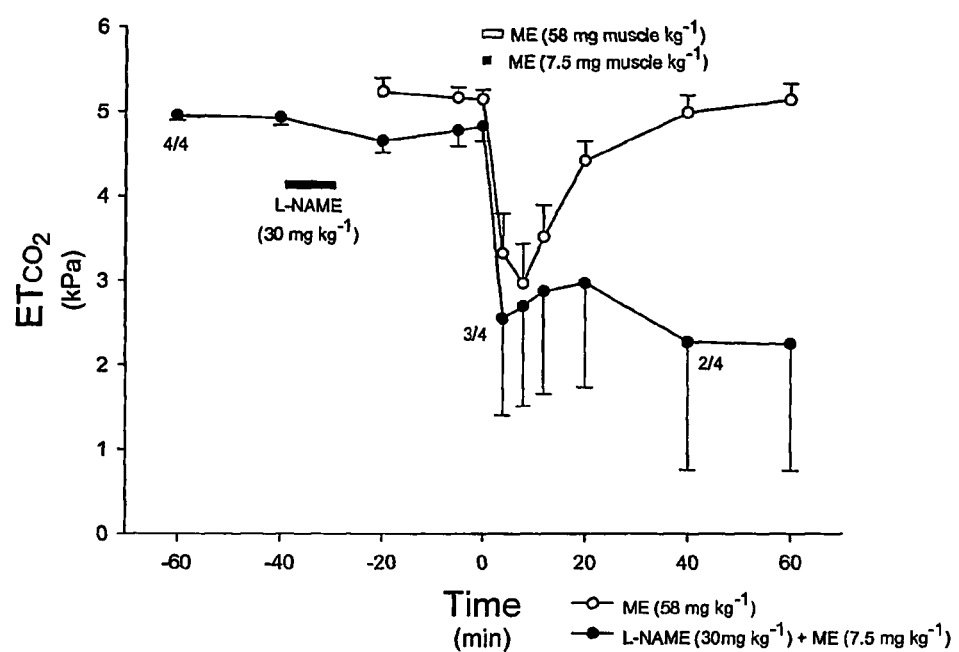
Figure 3:
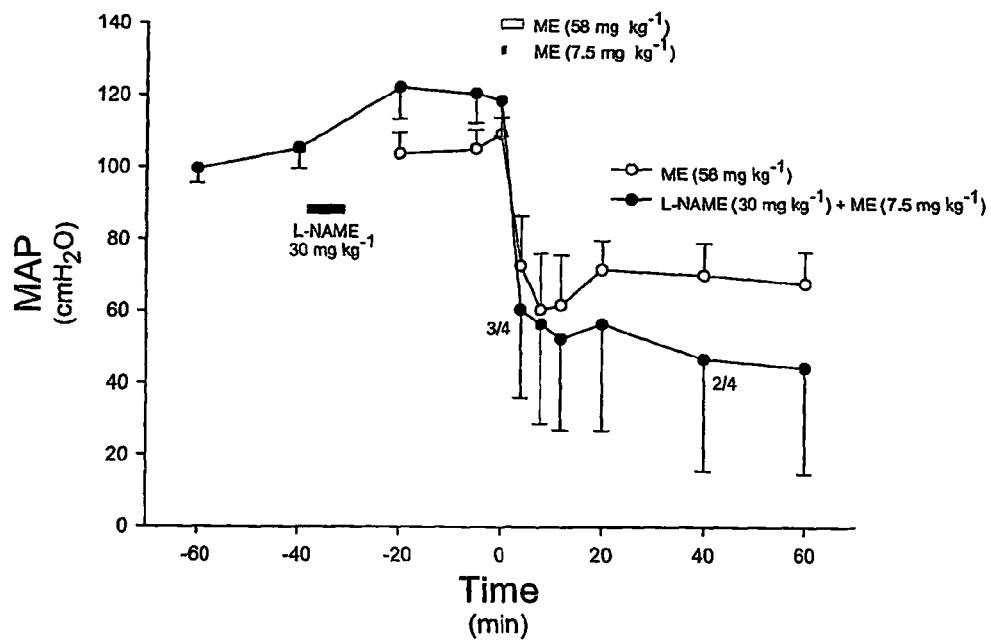
Figure 4:
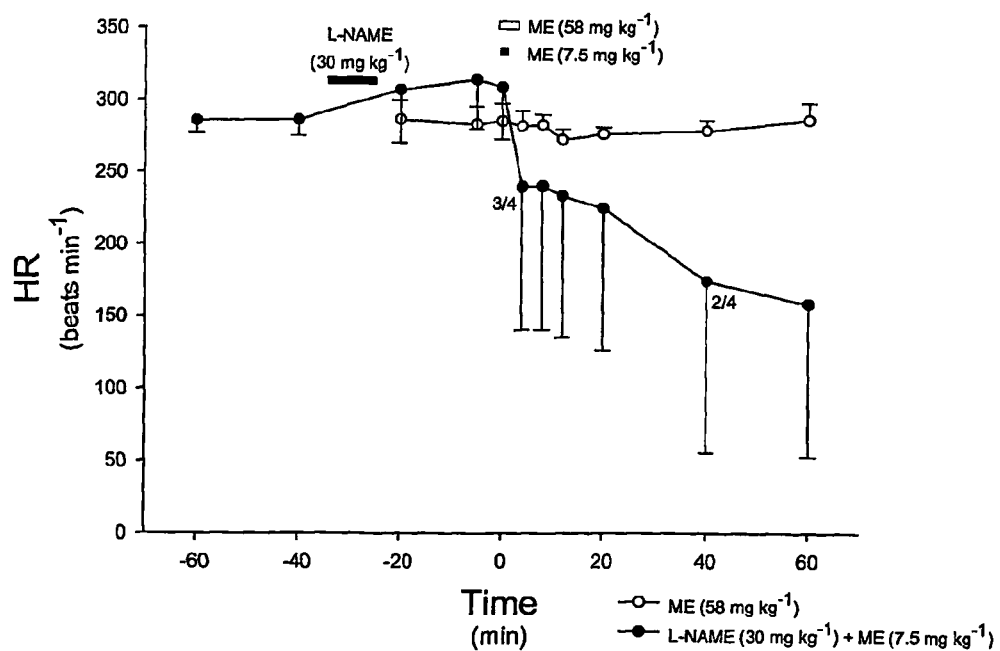
Figure 5:
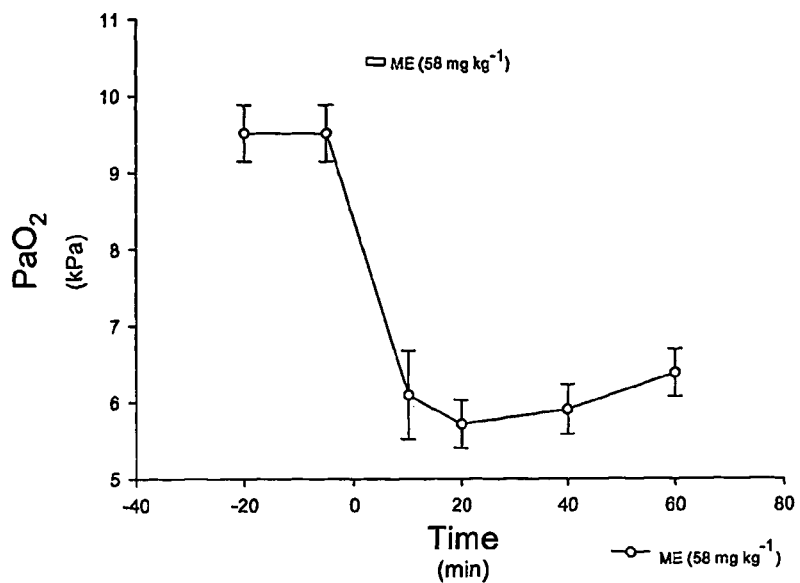
FIGS. 5 and 6 show arterial oxygen tension and haemoglobin oxygen saturation in rabbits challenged with Muscle embolus (unpretreated, 58 mg kg-1; n=6) as indicated by horizontal bar labeled ME.
Figure 6:
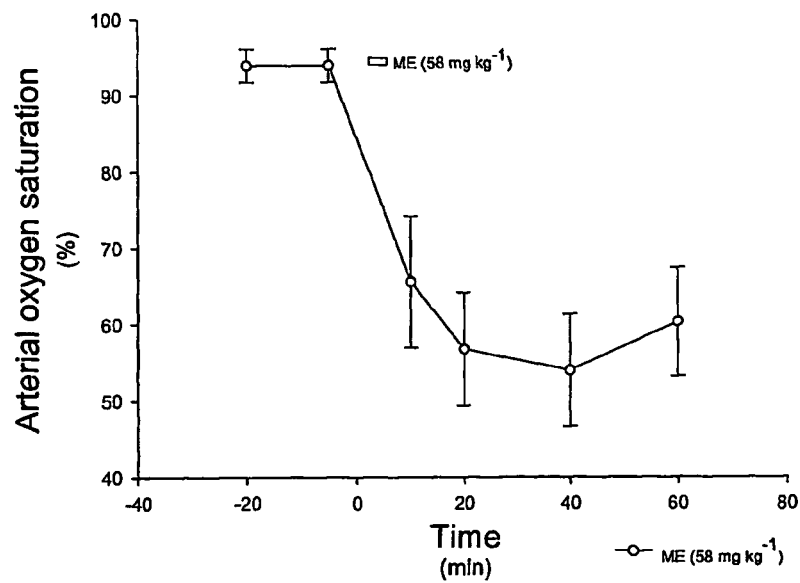
Figure 7:
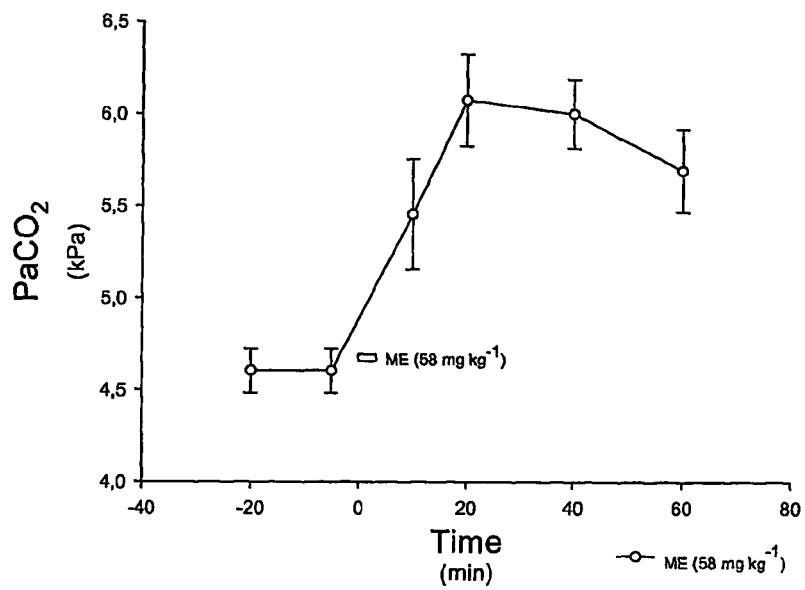
FIGS. 7 and 8 show arterial carbon dioxide tension and pH in rabbits challenged with muscle embolus (unpretreated, 58 mg kg-1; n=6) as indicated by horizontal bar labeled ME.
Figure 8:
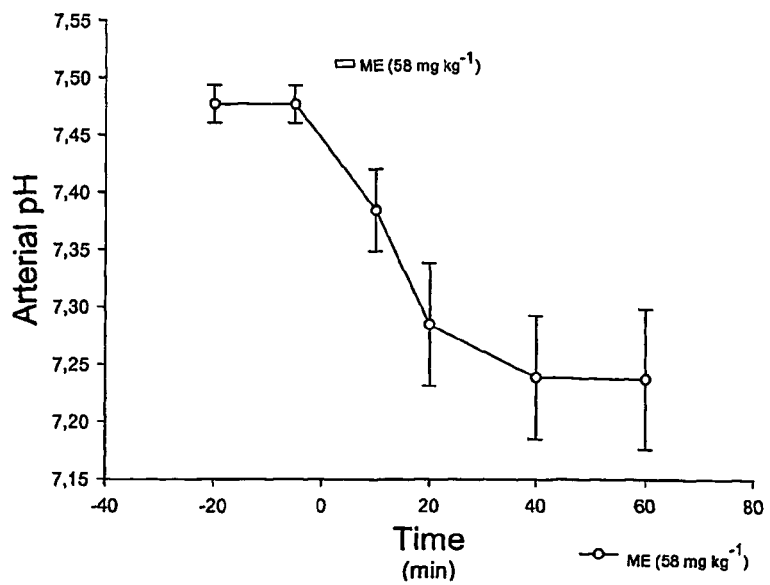

Rapid infusion (0.5 ml kg$^{-1}$ min$^{-1}$ during 30 min) of NO-gas dissolved in normal saline decreased MAP (from 128 $CmH_2O$ to 75 $CmH_2O$), increased HR (from 258 beats min$^{t1}$ to 295 beats mirf$^{1}$), and slightly increased exhaled nitric oxide (from 0 ppb to 2.5 ppb, FIG. 1). The metHb fraction increased dramatically (from 0.1% to 20%, FIG. 2). About 200 min after the infusion, the animal had almost completely recovered, and exhaled NO, MAP, HR and metHb were 0.8 ppb, 123 $CmH_2O$, 313 beats min$^{-1}$ and 2.5% respectively.

Infusion of NO-Gas Dissolved in Lipid Emulsion

Upon infusion (0.5 ml kg$^{-1}$ min$^{-1}$ during 30 min) of NO-gas dissolved in lipid emulsion exhaled NO increased (from 0.8 ppb to 32.5 ppb, FIG. 1), MAP fell from 106 $CmH_2O$ to 55 $CmH_2O$ while HR and metHb fraction (FIG. 2) were hardly affected.

Discussion on Intravenous Infusion of NO Dissolved in Liquid Medium

The results clearly show that the administration of NO, via the blood circulation to the lungs, dissolved in a liquid medium, is heavily increased (about 15 times), monitored as exhaled NO, when NO is dissolved in lipid emulsion compared to normal saline. The present inventors point out a noticeable disadvantage of dissolving NO in normal saline compared to lipid emulsion, in that metHb is greatly increased. Generation of metHb may be serious if arterial oxygen saturation is reduced, for example in conditions with pulmonary hypertension like pulmonary embolism. In this experiment, the present inventors used a very high infusion rate and therefore MAP decreased significantly, but believe that a much slower infusion rate is sufficient to generate beneficial effects in the lung in conditions with pulmonary hypertension or thromboembolism and may achieve this without causing a major decrease in the systemic arterial blood pressure. Notice that exhaled NO increased to 32.5 ppb from <1 ppb and that normal levels of NO in mixed exhaled breath is approximately 20 ppb. Further it might not be necessary to generate these levels in exhaled gas as the beneficial effects probably are on the vasculature. The magnitude of the fall in MAP could also partly be due to the inhibition of endogenous NO generation.

In another experiment, the present inventors successfully treated venous gas embolism with NO dissolved in lipid emulsion, in an animal with inhibited NO production, whereas it was impossible to treat the same condition with inhaled nitric oxide in the same experimental setting. The beneficial effects may be induction of vasodilation in the pulmonary vasculature, inhibition of aggregation of thrombocytes and/or minor vasodilation in the whole or parts of the systemic circulation, for example in the coronary circulation.

Animal Studies for The Evaluation of Capability to Deliver NO

The experiments were approved by the local animal ethics committee. Male white New Zealand rabbits were subjected to different doses of an intravenous infusion of NO-substituted solutions at different doses. Several physiological parameters were measured during the experiments, including NO concentration in mixed exhaled gas (FENO).

Anaesthesia and Initial Surgical Procedures

The animals were anaesthetized via an ear vein with sodium pentobarbital, 6 mg ml$^{-1}$ in saline, 40-60 mg kg$^{-1}$. The animals were placed in supine position and tracheotomised to allow mechanical ventilation, using a constant volume ventilator (model 683, Harvard Apparatus, South Natick, Mass., USA). The ventilator was supplied with NO-free air using a charcoal filter (110×11 cm). Respiratory rate was 40 min$^{-1}$, and tidal volume was initially adjusted to keep the end-tidal $CO_2$ ($ETcO_2$) at 4.5-5.3% as determined by a gas analyser (Oscar-Oxy, Datex, Helsinki, Finland), which sampled gas (150 ml min$^{-1}$, 15-20% of minute ventilation) from one of two side-arms connected to the tracheal cannula, and using a Naphion® sampling catheter. To the other side-arm a pressure transducer (Statham, Hato Rey, Puerto Rico)

was connected to monitor the insufflation pressure (IP). The gas from the ventilator outlet was led through a switching valve to either of two beakers creating a positive end-expiratory pressure (PEEP) of 1-2 $CmH_2O$ or 4-5 cmHaO. During the experiment the gas flow was altered between the lower PEEP (9 min) and the higher PEEP (1 min) with an interval of totally 10 min in order to optimise ventilation and prevent atelectasis formation. A continuous infusion containing glucose (24.3 g $l^{-1}$), dextran 70 (Makrodex® 26.5 g $l^{-1}$), $NaHCO_3$ (6.2 g $l^{-1}$), sodium pentobarbital (4.1 g $l^{-1}$) and pancuronium bromide (98 mg $ml^{-1}$) was administered at a rate of 5 ml $kg^{-1}$ $h^{-1}$ via the same ear vein by means of a Terumo STC-521 syringe pump (Terumo Corp., Tokyo, Japan). A heparinised catheter was inserted in the left common carotid artery for mean blood pressure (MAP) and heart rate (HR) recordings (Statham pressure transducer), and arterial blood sampling. Another catheter was inserted in the right jugular vein for administration of infusions. Body temperature was maintained at 38-38.5° C. by means of a heating pad connected to a thermostat. The animals were allowed a 30-60 min intervention-free period to obtain stable circulatory conditions and stable FENO-values.

NO Measurements in Exhaled Breath

FENO was continuously measured by means of a chemiluminescence-based system (NIOX®, Aerocrine AB, Solna, Sweden) sampling at 100 ml $min^{-1}$ at the end of a mixing chamber connected to the ventilator exhaust. The completeness of the mixing of expired air was intermittently checked by monitoring $CO_2$ concentration in the same chamber. Calibration was performed using certified NO standard gas in nitrogen (AGA Specialgas, Lidingö, Sweden).

Preparation of NO Substituted Solutions

Different carrier media solutions (table 1) were dissolved and diluted with saline or water to obtain different concentration of the solutions. The solution was then placed in a gas-tight chamber and deoxygenated by means of helium bubbling for 10 min. The glass chamber was then gassed with pure nitric oxide gas for 3-4 min.

Experimental Protocol

After the stabilisation period, the animals received intravenous infusions (CMA/100, Carnegie Medicine AB, Stockholm, Sweden) of the different solutions at different infusion rates into a saline carrier flow (864 Syringe Pump, Univentor LTD, Zejtun, Malta) of 100 µl $kg^{-1}$ $min^{-1}$ through the jugular vein catheter. Blood samples were collected and analyzed for blood gases and acid-base status (ABL 300, Radiometer A/S, Copenhagen, Denmark) intermittently. FENO, $ETCO_2$, HR, MAP and IP were continuously monitored on a Grass Polygraph (Grass Instruments Co, Quincy, Mass., USA) during the experiments.

Drugs

Heparin (Kabi Vitrum, Stockholm, Sweden), pancuronium bromide (Pavulon®, Organon, Oss, Holland), dextran 70 (Macrodex®, Pharmalink, Spanga, Sweden) and sodium pentobarbital (Apoteksbolaget) were purchased from Apoteksbolaget, Stockholm, Sweden. The other chemicals were from Sigma Chemical Co, St Louis, Mo., USA.

Statistical Analysis

Data are given as mean±SEM.

TABLE 1

Artificially-ventilated pentobarbital anesthetised rabbits (n = 1-4). Changes in mixed exhaled nitric oxide and mean arterial blood pressure (MAP) due to intravenous infusion d00uL/$kg^{-1}$ $min^{-1}$) of different carrier solutions saturated with pure nitric oxide gas.

| Carrier | Concentration (M) | Dose (mmol $kg^{-1}$ $min^{-1}$) | Pre-infusion values | Infusion values | Change (absolute value) | Change (%) | Number of animals |
|---|---|---|---|---|---|---|---|
| Saline | 0.153 | 0.0153 | | | | | 2 |
| Exhaled N O (ppb) | | | 11.7 | 11.7 | 0 | 0 | |
| MAP ($CmH_2O$) | | | 96.1 | 87.2 | −8.9 | −7.8 | |
| Glucose (60%) | 3.33 | 0.333 | | | | | 2 |
| Exhaled N O (ppb) | | | 15.5 | 21.7 | 6.3 | 40 | |
| MAP ($cmH_2O$) | | | 100 | 47.5 | −52.5 | −51 | |
| Fructose (60%) | 3.33 | 0.333 | | | | | 1 |
| Exhaled N O (ppb) | | | 14.9 | 28.0 | 13.1 | 88 | |
| MAP ($CmH_2O$) | | | 115.2 | 59.1 | −56.1 | −49 | |
| Galactose (60%) | 3.33 | 0.333 | | | | | 1 |
| Exhaled N O (ppb) | | | 7.9 | 11.2 | 3.3 | 41 | |
| MAP ($cmH_2O$) | | | 142.4 | 72.7 | −69.7 | −48.9 | |
| Glucosamine | 3.33 | 0.333 | | | | | 1 |
| Exhaled N O (ppb) | | | 10.3 | 9.3 | −0.9 | −9 | |
| MAP ($CmH_2O$) | | | 125.7 | 121.2 | −4.5 | −4 | |
| Arginine | 2.0 | 0.2 | | | | | 1 |
| Exhaled N O (ppb) | | | 21.2 | 21.8 | 0.6 | 3 | |
| MAP ($CmH_2O$) | | | 111.8 | 102.9 | −8.8 | −8 | |
| Sorbitol (60%) | 3.33 | 0.333 | | | | | 1 |
| Exhaled N O (ppb) | | | 7.0 | 11.2 | 4.2 | 60 | |
| MAP ($CmH_2O$) | | | 130.3 | 66.7 | −63.6 | −48.8 | |
| Mannitol (20%) | 1.11 | 0.111 | | | | | 1 |
| Exhaled N O (ppb) | | | 8.4 | 13.1 | 4.7 | 55.6 | |
| MAP ($CmH_2O$) | | | 127.3 | 66.7 | −60.6 | −48 | |
| Glucuronic acid | 3.33 | 0.333 | | | | | 1 |
| Exhaled N O (ppb) | | | 12.5 | 12.5 | 0 | 0 | |
| MAP ($cmH_2O$) | | | 82.4 | 64.7 | −17.6 | −21 | |
| Fucose | 0.609 | 0.0609 | | | | | 1 |
| Exhaled N O (ppb) | | | 18.8 | 22.9 | 4.1 | 22 | |
| MAP ($CmH_2O$) | | | 91.2 | 58.9 | −32.4 | −35 | |
| Ribose (50%) | 3.33 | 0.333 | | | | | 2 |
| Exhaled N O (ppb) | | | 12.1 ± 2.8 | 20.3 ± 0.2 | 8.2 ± 3.0 | 77 ± 43 | |
| MAP ($CmH_2O$) | | | 118.2 | 69.7 | −48.5 | −41 | |

TABLE 1-continued

Artificially-ventilated pentobarbital anesthetised rabbits (n = 1-4).
Changes in mixed exhaled nitric oxide and mean arterial blood pressure
(MAP) due to intravenous infusion dOOuL/kg$^{-1}$ min$^{-1}$) of different
carrier solutions saturated with pure nitric oxide gas.

| Carrier | Concentration (M) | Dose (mmol kg$^{-1}$ min$^{-1}$) | Pre-infusion values | Infusion values | Change (absolute value) | Change (%) | Number of animals |
|---|---|---|---|---|---|---|---|
| 2-deoxy-Ribose | 3.33 | 0.333 | | | | | 1 |
| Exhaled N O (ppb) | | | 12.1 | 44.8 | 32.7 | 269 | |
| MAP (cmH$_2$O) | | | 115.2 | 48.5 | −66.7 | −57.9 | |
| 1-O-methyl-Ribose | 3.33 | 0.333 | | | | | 1 |
| Exhaled N O (ppb) | | | 12.1 | 168 | 155.9 | 1284 | |
| MAP (cmH$_2$0) | | | 100.0 | 50.0 | −50.0 | −50 | |
| N-Acetylcysteine | 1.23 | 0.123 | | | | | 1 |
| Exhaled N O (ppb) | | | 21.2 | 25.3 | 4.1 | 19 | |
| MAP (CmH$_2$O) | | | 102.9 | 73.5 | −29.4 | −29 | |
| Glycerol | 3.33 | 0.333 | | | | | 4 |
| Exhaled N O (ppb) | | | 14.1 ± 1.3 | 77.4 ± 9.8 | 63.3 ± 10.5 | 475 ± 120 | |
| MAP (cmH$_2$O) | | | 110.3 ± 9.7 | 66.5 ± 6.8 | −43.7 ± 11.9 | −38 ± 7.7 | |
| 1,2-Propanediol | 3.33 | 0.333 | | | | | 1 |
| Exhaled N O (ppb) | | | 12.9 | 40.7 | 27.9 | 217 | |
| MAP (CmH$_2$O) | | | 94.1 | 79.4 | −14.7 | −16 | |
| 1,3-Propanediol | 3.33 | 0.333 | | | | | 1 |
| Exhaled N O (ppb) | | | 13.9 | 92.1 | 78.2 | 562 | |
| MAP (cmH$_2$0) | | | 114.7 | 76.5 | −38.2 | −33 | |
| 1-Propanol | 3.33 | 0.333 | | | | | 1 |
| Exhaled N O (ppb) | | | 12.9 | 107.1 | 94.3 | 733 | |
| MAP (CmH$_2$O) | | | 92.6 | 82.4 | −10.3 | −11 | |
| 2-Propanol | 3.33 | 0.333 | | | | | 1 |
| Exhaled N O (ppb) | | | 12.9 | 192.9 | 180 | 1400 | |
| MAP (CmH$_2$O) | | | 98.5 | 83.8 | −14.7 | −15 | |
| Alanine | 1.11 | 0.111 | | | | | 1 |
| Exhaled N O (ppb) | | | 20.8 | 20.8 | 0 | 0 | |
| MAP (CmH$_2$O) | | | 97.1 | 97.1 | 0 | 0 | |
| 2-Amino-1,3-propanediol | 3.33 | 0.333 | | | | | 1 |
| Exhaled N O (ppb) | | | 17.3 | 19.6 | 2.4 | 14 | |
| MAP (cmH$_2$O) | | | 77.9 | 64.7 | −13.2 | −17.0 | |
| 3-Amino-1,2-propanediol | 3.33 | 0.333 | | | | | 1 |
| Exhaled N O (ppb) | | | 20.2 | 20.2 | 0 | 0 | |
| MAP (cmH$_2$O) | | | 73.5 | 73.5 | 0 | 0 | |
| Lactate | 3.33 | 0.333 | | | | | 1 |
| Exhaled N O (ppb) | | | 16.7 | 16.7 | 0 | 0 | |
| MAP (CmH$_2$O) | | | 88.2 | 86.8 | −1.5 | −2 | |
| Etanol | 3.33 | 0.333 | | | | | 1 |
| Exhaled N O (ppb) | | | 17.1 | 17.1 | 0 | 0 | |
| MAP (cmH$_2$O) | | | 82.4 | 82.4 | 0 | 0 | |
| Glycine | 1.23 | 0.123 | 16.2 | 15.6 | −0.6 | −4 | 1 |
| Exhaled N O (ppb) | | | 105.9 | 108.8 | 2.9 | 3 | |
| MAP (cmH$_2$O) | | | | | | | |
| Sucrose (60%) | 1.67 | 0.167 | | | | | 1 |
| Exhaled N O (ppb) | | | 14.9 | 26.1 | 11.2 | 75 | |
| MAP (cmH$_2$O) | | | 127.3 | 71.2 | −56.1 | −44 | |
| Lactobionic acid | 1.11 | 0.111 | | | | | 1 |
| Exhaled N O (ppb) | | | 19.6 | 28.0 | 8.3 | 42 | |
| MAP (cmH$_2$0) | | | 91.2 | 58.8 | −32.4 | −35 | |
| Polyethylene glycol | 3.33 | 0.333 | | | | | 1 |
| Exhaled N O (ppb) | | | 18.2 | 29.4 | 11.2 | 61 | |
| MAP (cmH$_2$0) | | | 91.2 | 73.5 | −17.6 | −19 | |
| Inulin (15%) | 0.03 | 0.003 | | | | | 1 |
| Exhaled N O (ppb) | | | 14.9 | 16.7 | 1.8 | 12 | |
| MAP (CmH$_2$O) | | | 85.3 | 58.8 | −26.5 | −31 | |
| Dextran (15%) | 0.00093 | 0.000093 | | | | | 1 |
| Exhaled N O (ppb) | | | 11.7 | 14.5 | 2.8 | 24 | |
| MAP (cmH$_2$0) | | | 131.8 | 86.4 | −45.5 | −34 | |
| Heparin (15000 IU/ml, 10%) | 0.0056 | 0.00056 | | | | | 1 |
| Exhaled N O (ppb) | | | 12.5 | 11.9 | −0.6 | −5 | |
| MAP (CmH$_2$O) | | | 72.1 | 63.2 | −8.8 | −12 | |
| Fucoidan (10%) | | | | | | | 1 |

TABLE 1-continued

Artificially-ventilated pentobarbital anesthetised rabbits (n = 1-4).
Changes in mixed exhaled nitric oxide and mean arterial blood pressure
(MAP) due to intravenous infusion dOOuL/kg$^{-1}$ min$^{-1}$) of different
carrier solutions saturated with pure nitric oxide gas.

| Carrier | Concentration (M) | Dose (mmol kg$^{-1}$ min$^{-1}$) | Pre-infusion values | Infusion values | Change (absolute value) | Change (%) | Number of animals |
|---|---|---|---|---|---|---|---|
| Exhaled N O (ppb) | | | 20.6 | 25.3 | 4.7 | 23 | |
| MAP (CmH$_2$O) | | | 107.4 | 51.5 | −55.9 | −52 | |
| Albumin (20%) | | | 16.2 | 16.7 | 0.6 | 4 | 1 |
| Exhaled N O (ppb) | | | 105.9 | 73.5 | −32.4 | −31 | |
| MAP (cmH$_2$O) | | | | | | Exhaled N O (ppb) MAP (cmH$_2$O) | |

The results show that many of the tested compounds function as selective NO carriers and support the generalizations presented in the claims. Compared to the saline control, glucose, fructose, galactose, ribose, sorbitol, mannitol, fucose, 2-deoxy-ribose, 1-O-methyl-ribose, sucrose, lactobionic acid, insulin, dextran, fucoidan, 1-propanol, 2-propanol, 1,2-propanediol, 1,3-propanediol, glycerol, polyethylene glycol, N-acetyl-cysteine, and albumin exhibited a noticeable effect.

When unsubstituted L-cysteine was deoxygenated and exposed to NO gas, a copious precipitate, unsuitable for infusion, was formed.

When short chain alcohols were tested, a marked effect was recorded for 1-propanol and 2-propanol. Also the compounds 1,2-propanediol and 1,3-propanediol exhibited NO delivering capacity in the experiments.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto.

REFERENCES

Abman S H, Chatfield B A, Hall S L & McMurtry I F (1990). Role of endothelium-derived relaxing factor during transition of pulmonary circulation at birth. Am J. Physiol. 259: H 1921-7

Deem et al., Anesthesiology., 1999 December; 91(6):1861-72

Gustafsson L E, Leone A M, Persson M G, Wiklund N P & Moncada S (1991). Endogenous nitric oxide is present in the exhaled air of rabbits, guinea pigs and humans. Biochem Biophys Res Commun. 181: 852-7.

Heymann M A (1999). Control of the pulmonary circulation in the fetus and during the transitional period to air breathing. Eur J Obstet Gynecol Reprod Biol. 84: 127-32

Persson M G, Gustafsson L E, Wiklund N P, Moncada S & Hedqvist P (1990). Endogenous nitric oxide as a probable modulator of pulmonary circulation and hypoxic presser response in vivo. Acta Physiol Scand. 140: 449-57

Priebe, Am. J. Physiol. 255 (Heart Circ. Physiol, 24):H1232-H1239, 1998

Rimeika D et al., Am J Respir Crit. Care Med 2004

Stamler J S, Loh E, Roddy M A, Currie K E & Creager M A (1994). Nitric oxide regulates basal systemic and pulmonary vascular resistance in healthy humans. Circulation. 89: 2035-40.

Tanus-Santos J E & Theodorakis M J (2002). Is there a place for inhaled nitric oxide in the therapy of acute pulmonary embolism?, Am J Respir Med. 1: 167-76.

The invention claimed is:

1. A non-gaseous composition for the delivery of gaseous nitric oxide (NO), comprising a compound bonded to NO, wherein said composition contains substantially no oxygen, wherein said compound is 1,2-propanediol or 1,3-propanediol.

2. The non-gaseous composition according to claim 1, wherein said composition is formulated as a lipid emulsion.

3. The non-gaseous composition according to claim 1, formulated for topical, rectal, vaginal, urethral, intravesical, nasal, ocular, sublingual, buccal, oral, enteral, intravenous, intraarterial, intratracheal, intramuscular or subcutaneous administration.

* * * * *